(12) United States Patent
Kalal et al.

(10) Patent No.: US 6,542,229 B1
(45) Date of Patent: Apr. 1, 2003

(54) SENSORS, METHODS OF MANUFACTURE AND SENSING METHODS

(76) Inventors: Peter J. Kalal, 120 W. Fourth St., Corning, NY (US) 14830; Mark A. Quesada, 3 Ambrose Dr., Horseheads, NY (US) 14845

( * ) Notice: Subject to any disclaimer, the term of this patent is extended or adjusted under 35 U.S.C. 154(b) by 0 days.

(21) Appl. No.: 09/950,815

(22) Filed: Sep. 12, 2001

(51) Int. Cl.$^7$ .............................................. G01N 21/41
(52) U.S. Cl. ..................... 356/128; 436/164; 422/82.05
(58) Field of Search .................. 356/128, 129, 356/133; 436/528, 518, 525, 807, 806, 904, 805; 435/7.1, 7.5, 7.21, 7.94; 422/82.02, 82.11, 82.05, 82.06, 82.07

(56) References Cited

U.S. PATENT DOCUMENTS

| | | | |
|---|---|---|---|
| 4,099,878 A | * | 7/1978 | Lee .............................. 356/128 |
| 5,648,269 A | * | 7/1997 | Lakowicz et al. ............. 436/68 |
| 5,811,312 A | * | 9/1998 | Hasegawa et al. ........... 436/527 |
| 5,955,379 A | * | 9/1999 | Lennox et al. ................ 436/528 |
| 6,149,868 A |  | 11/2000 | Natan et al. ............... 422/82.05 |
| 6,286,222 B1 |  | 7/2001 | Chandler et al. ............ 436/523 |
| 6,274,323 B1 |  | 8/2001 | Bruchez et al. ................ 435/6 |
| 6,436,651 B1 | * | 8/2002 | Everhart et al. ............ 435/7.21 |

OTHER PUBLICATIONS

Penner, Hybrid Electrochemical/Chemical Synthesis of Quantum Dots, Acc. Chem. Res, Vo. 33, No. 2, pp 78–86 (2000).
Anderson, MA et al., A hybrid Electrochemical/Chemical Synthesis of Supported, Luminescent Cadmium Sulfide Nanocrystals, J. Phys. Chem. B, 101, pp. 5895–5899 (1997).
Zoval, J.V., Electrochemical Deposition of Silver Nanocrystallites on the Atomically Smooth Graphite Basal Plane, J. Phys. Chem. 100, pp. 837–844 (1996).
Alivistos, Perspectives on the Physical Chemistry of Semiconductor Nanocrystals, J. Phys Chem, 100, pp. 13226–13239 (1996).

* cited by examiner

*Primary Examiner*—Hao Q. Pham
(74) *Attorney, Agent, or Firm*—Scott S. Servilla

(57) ABSTRACT

Optical sensors and methods are disclosed. The resonance energy transfer between a donor and acceptor pair on a surface is monitored. The change in resonance energy transfer as a function of the change in refractive index of a sensing area disposed between the donor and acceptor pair is utilized to provide various sensing methods and structures.

20 Claims, 2 Drawing Sheets

WAVELENGTH (λ)

SENSORS, METHODS OF MANUFACTURE AND SENSING METHODS

FIELD OF THE INVENTION

This invention relates to sensing. More particularly, the present invention relates to apparatus and methods for sensing refractive index changes by monitoring the energy transfer between a chromophore acceptor and a donor.

BACKGROUND OF THE INVENTION

Optical sensors, including sensors that monitor absorbance changes and refractive index changes proximate a sensing area are used in the fields of chemical, biochemical, biological or biomedical analysis, process control, pollution detection and control, and other areas. Luminescent (including fluorescent and phosphorescent) markers also find a wide variety of applications in science, medicine and engineering. These sensors and techniques are adaptable to a wide variety of samples including biological samples and extracts (such as physiological fluids, nucleic acid and/or protein-containing solutions, microbial cultures, etc.), environmental samples (such as water sources), industrial, especially chemical reagents, products and wastes, etc.

Surface-plasmon resonance (SPR) is a popular sensing technique in the pharmaceutical industry and biological research. SPR is but one of a large class of optical biosensors collectively referred to as evanescent wave-based detectors. This class includes film waveguide grating couplers, film prism waveguide couplers and long-period grating waveguide couplers. The essential feature of all these techniques is that a standing "evanescent" wave is generated above the sensing surface by a short wavelength's distance from the surface (approximately 100–200 nm) that is sensitive to the local dielectric environment. By changing the local refractive index, the standing wave is altered, requiring either a new angle of incident light to set up the "resonance condition" or inducing a phase shift of the reflected light. Since all proteins, independent of sequence, contribute almost the same refractive index per unit mass, this technique can serve as a mass detector. A linear correlation between resonance angle shift and surface protein concentration has been demonstrated, allowing real time detection of mass change without the need for labeling. All evanescent wave techniques are variations on this essential theme.

One limitation of evanescent wave methods is that they do not readily lend themselves to miniaturization. This limitation makes massive deployment of similar sensing elements on small surfaces extremely problematic. Another limitation of these techniques is that the sensitivity of these optical sensors is limited by many factors such as signal to noise ratio such that the sensitivity of these techniques are usually limited to about $10^{-5}$ or $10^{-6}$ Moles/liter in the sensing area.

Another known sensing technique is the monitoring of the energy transfer between a luminescent donor-acceptor pair as a function of the changing distance between the donor-acceptor pair. Luminescent structures are either man-made (see, e.g., Alivisatos, A. P., "Perspectives on the Physical Chemistry of Semiconductor Nanocrystals," Journal of Physical Chemistry, 100, 31, pp. 13226–13239 (1996); Chan, W. C. and Nie, S., "Quantum Dot Bioconjugates for Ultrasensitive Nonisotopic Detection," Science, 281, pp. 2016–2018, (1998); Davies, J. H. and Long, A. R. (eds.), Physics of Nanostructures," St. Andrews, Institute of Physics Publicshing Ltd., (1992)) or naturally occurring (see, e.g., Glazer, A. N. and Mathies, R. A., "Energy-transfer fluorescent reagents for DNA analyses, "Current Opinions in Biotechnology," 8 (1), pp. 94–102, (1997); Yardley, J. T., "Introduction to Molecular Energy Transfer," New York, Academic Press (1980). An example of a man-made structure is a semiconductor sandwich (e.g., GaAs disposed between AlGaAs layers), which shares all of the attributes of a transition dipole structure that both absorbs and emits light and is directional. For more details on these structures, refer to the Chan and Nie and Davies references, the entire contents of which are incorporated herein by reference. These structures, which may be referred to as quantum dots, quantum wires, quantum well structures, or nanocrystals, can be coated to stabilize them in various solutions. More commonly, however, luminescent pairs of donors and acceptors typically include luminescent molecules such as dyes or lanthanides having light absorption and emission properties. For a review of Fluorescent Resonance Energy Transfer, see, Selvin (1994) Fluorescence Resonance Energy Transfer, in Biochemical Spectroscopy, a volume of Methods in Enzymology, Academic Press, Ed. Kenneth Sauer.

U.S. Pat. No. 5,639,615 describes measuring luminescent energy transfer between lanthanide chelate acceptor-donor pairs. The resonance energy transfer described in U.S. Pat. No. 5,639,615 involves detecting the distance between a donor and an acceptor in a portion of a sample by exposing a sample including the donor located at a first position and the acceptor located at a second position to light at a first wavelength capable of inducing a first electronic transition in the donor. The spectral overlap of the donor emission and acceptor absorption is sufficient to enable energy transfer from the donor to the acceptor as measured by a detectable decrease of donor luminescence intensity or a detectable increase in acceptor luminescence intensity. Then the intensity of a first emission of light from the sample portion at a second wavelength is detected, which results from a second electronic transition in the donor. The intensity of the first emission of light correlates with the distance between the first and second positions. In other words, the closer the positions, the greater the energy transfer and the greater the decrease in energy emitted from the donor. An alternative scheme described in U.S. Pat. No. 5,639,615 involves the detection of the intensity of a second emission of light from sample portion at a third wavelength, in which the third wavelength is longer than the first wavelength and results from an electronic transition in the acceptor. The intensity of the second emission of light inversely correlates with the distance between the first and second positions of the sample portion. Thus, the closer the positions, the greater the energy transfer and the greater the acceptor luminescence.

The general method described in U.S. Pat. No. 5,639,615 may be used to measure the static or dynamic distance between two positions, for example, two atoms or molecules. In particular, the method can be used to monitor the status of a polymerase chain reaction. In this instance, the sample portion may include a target nucleic acid strand having a first strand portion and a probe nucleic acid strand labeled proximal to one end with the acceptor and proximal to the other end with the donor. Thus, the donor and the acceptor are separated from each other by the opposite ends of the second strand. The first and second strands are sufficiently complementary to hybridize under annealing conditions. If the second strand is of sufficient length to provide a detectable difference in the aggregate energy transfer from the donor to the acceptor upon hybridization of the first and second strands, as compared with the aggregate energy transfer from the donor to the acceptor when the first and second strand portions are not hybridized, a detectable difference in energy transfer can be measured. The detectable difference is measured as at least one of a detectable decrease or quenching of donor luminescence or detectable increase in acceptor luminescence, and the distance between the acceptor and donor, as a function of changing luminescence, indicates whether the nucleic acid strands have hybridized. Thus, as the reaction proceeds, the stepwise increase in the amount of target nucleic acid is reflected in a stepwise decrease in energy transfer.

The sensitivity of methods using resonance energy transfer as a function of the changing distance between the donor-acceptor pair can be as high as $10^{-12}$ Moles/liter. Although these conventional resonance energy transfer techniques have many advantages, they rely on the change in distance between the donor and the acceptor pair to determine the energy transfer between the donor and the acceptor. It would be advantageous to provide a sensor and sensing methods that provide the advantages of optical sensing techniques discussed above and have the sensitivity of the conventional resonance energy transfer techniques. It would also be desirable to provide a sensing technique that facilitates the miniaturization of the sensor and could be deployed on a wide variety of surface and in various environments.

SUMMARY OF INVENTION

The invention relates to a sensor and methods of sensing. According to one aspect of the invention, a sensor includes a donor for emitting energy and an acceptor for receiving energy. According to this aspect, a sensing area is disposed between the donor and the acceptor, and a photon source for directing photons towards the donor. A detector is also provided for monitoring energy transfer between the acceptor and the donor as a function of the change in refractive index proximate the sensing area. The donor and acceptor can be any luminescent material capable of functioning as an acceptor-donor energy transfer pair. For example, the donor and the acceptor may include dye molecules or atoms, or alternatively, the donor and the acceptor may include a semiconductor crystal, quantum dot, quantum wire or quantum well structure. These terms will be referred to herein as either semiconductor crystal or quantum well structures. In another aspect, the donor and the acceptor may include fluorescent beads or fluorescent proteins, or other luminescent chromophores having a non-zero transition dipole moment. According to one aspect of the invention, the sensor is adapted to detect interactions between biomolecules, or between biomolecules and other chemical entities.

In another aspect of the invention, a method of sensing the refractive index change is provided. According to this aspect, the method includes monitoring the Förster resonance energy transfer between an acceptor and a donor. As with the sensor described above, the acceptor and the donor may include a semiconductor crystal, atom, a quantum well structure, a fluorescent dye, a protein or a fluorescent bead.

Another aspect of the invention pertains to a method of sensing interaction between biomolecules or between biomolecules and other chemical entities. This aspect includes providing an acceptor and donor pair having a sensing area disposed between the pair and providing biomolecules proximate the sensing area. According to this aspect, photon energy is directed towards the donor and the transfer of photon energy between the donor and the acceptor is monitored as a function of refractive index proximate the sensing area.

Still another aspect of the invention relates to biosensor that includes a substrate having a donor and acceptor pair disposed on a surface of the substrate and a sensing area disposed between the donor and the acceptor. According to this aspect, a photon source for directing photon energy towards the donor and means for detecting energy transfer between the donor and the acceptor are provided. This aspect of the invention further includes means for correlating the energy transfer with a change in refractive index proximate the sensing area. In one embodiment of the invention, the biosensor substrate may include a variety of structures that are used in biomolecular analysis. For example, the substrate may a microplate well, a slide including biomolecules attached thereto, or a microfluidics channel.

Another aspect of the invention pertains to a method of manufacturing a sensor. This aspect includes providing an acceptor, a donor and a sensing area disposed between the acceptor and the donor on a surface and directing energy towards the donor. This aspect further includes contacting the sensor with a solution and monitoring the energy transfer between the acceptor and the donor as a function of the change in refractive index of the sensing area.

The invention provides sensing methods and sensors having extremely high sensitivity and the ability to be deployed on a wide variety of surfaces. The sensors and sensing methods of the present invention can be used to sense in a wide variety of environments in which the refractive index of a sensing surface or area changes. For example, the sensing methods and sensors described herein can be used to sense chemical reactions and biomolecular reactions.

Additional advantages of the invention will be set forth in the following detailed description. It is to be understood that both the foregoing general description and the following detailed description are exemplary and are intended to provide further explanation of the invention as claimed.

DETAILED DESCRIPTION

The present invention relates to sensors and methods of sensing by sensing changes in the refractive index changes on a sensing substrate with extremely high sensitivity. The methods and sensors of the present invention do not require labeling of samples by the end-user. The change in the refractive index of a sensing area disposed between a donor and acceptor pair is utilized to detect the presence or absence of a species is monitored by detecting a disruption in the Förster resonance energy transfer. The invention is widely adaptable to a variety of sensing applications, including, but not limited to, clinical, forensics, genetic analysis, biomolecular analysis and drug-discovery efforts.

The present invention involves placing a pair of luminescent structures in close proximity and illuminating one of the pair of structures so that Förster resonance energy transfer (FRET) occurs as incident photon energy flows between the adjacent structures. FRET is dependent on the inverse sixth power of the donor-acceptor separation, and has found use over distances comparable with the dimensions of biological macromolecules. According to the present invention however, the distance between the acceptor and the donor remains fixed while the refractive index change between the donor and the acceptor is monitored as related to the changing luminescence from the donor-acceptor pair.

The expression derived by Förster for the rate of energy transfer ($k_{if}$) from the excited state of a donor to an acceptor may be expressed as follows:

$$k_{if} = \frac{2\Pi K^2 \mu_{Dif}^2 \mu_{Aif}^2}{n^4 h^2 r^6} \int g_{abs}^A(\omega) g_{em}^D(\omega) d\omega \quad (1)$$

Figure 1:
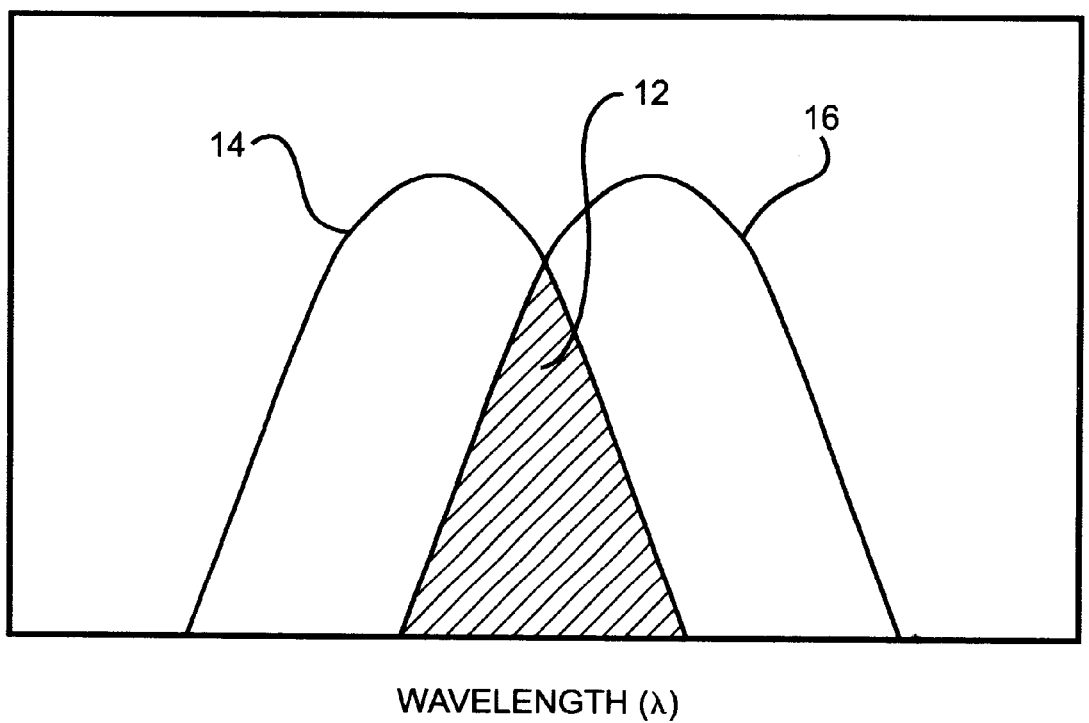
FIG. 1 shows the spectral overlap between a donor and an acceptor.

In this equation, r is the distance between the donor and the acceptor structures, and the integral is the spectral overlap integral (for convenience, hereinafter referred to a J). Referring to FIG. 1, J represents a value related to the overlap 12 of the donor's emission spectra 14 and the acceptors absorption spectra 16. Because the transfer is assumed to result from the coupling of dipole oscillators, the probability of transfer is at a maximum when the donor and acceptor dipoles are parallel, and zero when the dipoles are at right angles. K is an orientation factor, and for random orientation between the donor and acceptor, the average value of $K^2$ is two-thirds. The refractive index, n, is the refractive index of the material between the acceptor and the donor. The transfer rate is proportional to the strength of the donor dipole moment, $\mu_{Dif}$, and to the strength of the acceptor dipole moment, $\mu_{Aif}$. The term $g^A{}_{abs}$ refers to the absorption spectrum of the acceptor, gD em refers to emission spectrum of the donor, h is Planck's constant AND $\omega$ is the frequency as an independent variable.

It is convenient to describe a critical radius $R_o$ that separates the acceptor and donor so that:

$$k_{if} = \frac{(R_0/R)^6}{\tau_D}, \quad R_0^6 = \frac{2\Pi K^2 c^3 \mu_{Aif}^2 \mu_{Dif}^2}{3n^5 h \omega^3} J \quad (2)$$

where R (in angstroms) is again the donor-acceptor separation distance, $\tau_D$ is the luminescent lifetime of the donor and $R_0$ is the donor-acceptor distance at 50% transfer efficiency. Because of the $R^6$ dependence, the transition rate rapidly decreases to zero when R is greater than $R_0$. Furthermore, the transition rate depends sensitively on the refractive index of the medium intervening between the donor and the acceptor.

To engineer acceptor and donor pairs that will transfer photon energy by Förster energy transfer over a variety of distances, the parameters $\mu_{Aif}$, K, $\omega$, and J can be optimized. For example, material may be selected that have large dipole moments, and these materials can be oriented such that they operate in the far infra-red wavelength range and have excellent spectral overlap integrals that result in FRET transfer over large distances. As one example, if the acceptor and the donor are a semiconductor crystal or quantum well structure, these parameters may be estimated by using a quantum well interband subband dipole moment of 86 Debye. The relative orientation of both structures can be made perfectly parallel to one another resulting in the orientation factor, K~1 (see, Yardley, J. T., "Introduction to Molecular Energy Transfer," New York, Academic Press (1980), the contents of which are incorporated herein by reference). The photon frequency involved in the transfer can be produced with quantum wells operating at much lower frequencies operating in the area of $\omega$~12,500 $cm^{-1}$. The emission spectral line width of quantum well acceptor-donor structures has been measured at approximately one-third that of fluorescent molecules (see, Chan, W. C. and Nie, S., "Quantum Dot Bioconjugates for Ultrasensitive Nonisotropic Detection," Science, 281, pp. 2016–2018, (1998), the contents of which are incorporated herein by reference).

Considering the fact that the critical radius, $R_0$, for fluorescent molecules is typically on the order of 34 angstroms and the critical radius, $R_0$, for a quantum well structure is on the order of 355 angstroms, it is evident that the range of Förster resonance energy transfer can be increased by over an order of magnitude when constructing the acceptor-donor pair from semiconductor crystals or quantum wells. These dimensions accommodate typical biomolecules that should sensitively affect the amount of Förster energy that is transferred between an acceptor and a donor, thus signaling the presence or absence of the biomolecule in a sensing area disposed between the acceptor and donor pair. Furthermore, the structure will detect changes in refractive index caused by either binding or association of any chemical entity to the biomolecules present or matter moving through the sensing area.

Figure 2:
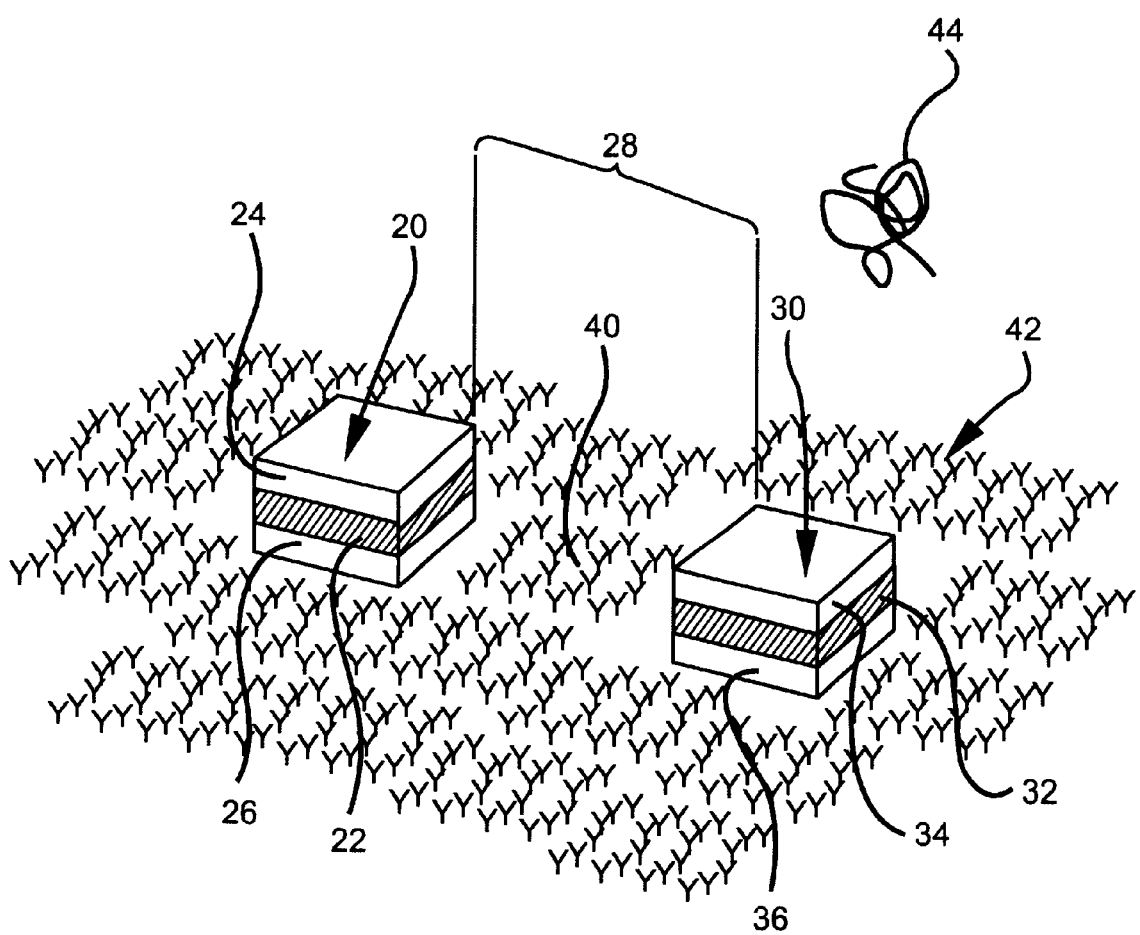
FIG. 2 shows a schematic representation of sensor according to one embodiment of the invention.

An example of a semiconductor crystal or quantum well structure capable of sensing the presence or absence of a biomolecule disposed between the donor-acceptor pair could include ZnS capped CdSe quantum wells that are grown on a surface 35 nm apart. Referring now to FIG. 2, a donor 20, comprising a quantum well structure including a first region 22 made from materials such as CdSe or any other appropriate material capped by regions 24 and 26 and made from a material such as ZnS or any other appropriate material can be place on a substrate surface 28. An acceptor 30, including a first region 32, made from an appropriate material such as, for example, CdSe, is capped by regions 34 and 36, which are made from an appropriate material such as ZnS to provide a quantum well structure is placed on the substrate surface 28, and spaced from the donor at an appropriate distance to enable energy transfer when the quantum well structure is illuminated by a photon source.

According to one aspect of the invention, a biosensor can be provided by disposing an acceptor-donor pair as shown in FIG. 2 on the surface 28 of the substrate. A sensing area 40 is provided between the donor 20 and the acceptor 30. A first biomolecule 42, such as, for example, antibodies, can be provided on the surface 28, including on the sensing area 40. When a second biomolecule 44, for example, a protein, binds to the first biomolecules 42 in the sensing area 40, the refractive index of the sensing area 40 will change, and the magnitude of the Förster energy transfer between the donor 20 and the acceptor 30 is modulated. This modulation in energy transfer will change the intensity or spectral distribution of the luminescence emitted from the donor-acceptor pair, which can be detected by an appropriate detector.

It will be understood by those skilled in the art that the substrate can include any suitable substrate to provide a surface that the donor and acceptor pair can be associated with. For example, the substrate could be a planar piece of material such as a microscope slide. Advantageously, the ability to manufacture relatively small acceptor-donor pairs facilitates placing acceptor-donor pairs on a wide variety of structures such as on the surface or embedded in microfluidics devices, microarrays used in biomolecular analysis and microplate wells.

The donor-acceptor pair can be illuminated with any appropriate illumination source, which will depend on the type of acceptor-donor pair (i.e., whether the acceptor-donor pair is a quantum well structure, a dye or some other material). For example, the photon source may include a continuous wave laser, a laser diode or a similar illumination device known to those skilled in the art. Preferably, the incident photon is provided in a form to minimize background absorption. Example of such useful sources include lasers, such as nitrogen, helium-cadmium, and dye lasers and arc lamps such as high-pressure, mercury, xenon, and quartz.

Similarly, an appropriate detector for detecting the change in emission of photons by the acceptor-donor pair as a function of the change in refractive index can be selected by a person skilled in the art. For example, a suitable detector may include a charge-coupled device (CCD) camera or photomultiplier tube (PMT), which can be connected to appropriate processing equipment, such as a computer utilizing software, to correlate the change in luminescence with the change in refractive index proximate the sensing area disposed between the donor-acceptor pair. The detector should be have low background noise, and it should have a high enough quantum efficiency in the spectral emission region of the acceptor. This change in refractive index can be determined by solving equation (1) above. Since each of the parameters of equation (1) is known for an acceptor donor system, and the distance between the acceptor and donor is fixed, the change in refractive index can be determined by solving equation (1). According to another aspect of the invention, a detector can be selected to monitor the change in the shape of the emission spectrum of the donor-acceptor pair. This change in spectral overlap can then be used to determine the change in refractive index proximate the sensing area.

Various donors and acceptors may be utilized according to the present invention. The donors and acceptors must be capable of resonance energy transfer between the donor and the acceptor when the donor is illuminated by a photon source. Such acceptor-donor pairs can include, but are not limited to, quantum well structures, atoms, luminescent dyes, fluorescent biomolecules such as fluorescent proteins, and rare earth phosphorescent materials. Suitable fluorescent donors and acceptors may include xanthene dyes such as fluoresceins and rhodamines, cyanine dyes, coumarins such as umbelliferone, benzimide dyes such as Hoechst 33258, phenanthridine dyes such as Texas Red, ethidium dyes, acridine dyes, carbazole dyes, phenoxazine dyes, pophyrin dyes and quinoline dyes. More specific examples of suitable dyes may be found in U.S. Pat. No. 6,150,107, the contents of which are incorporated herein by reference.

Other suitable donor-acceptor pairs may include lanthanides and lanthanide chelates. While lanthanides do not fluoresce, lanthanide chelates can be excited. A non-fluorescent quantum transition of the lanhandide can then effect a non-radiative energy transfer to a suitable and appropriately distanced acceptor. To effect transfer, an acceptor absorbtion must overlap a lanthanide emission. The chelate—acceptor pair is selected for optimal overlap: for longer distance measurements, greater overlap is preferred. Since the lanthanides have lifetimes on the order of milliseconds, the signal-to-noise ratio of sensitized emission of the acceptor is improved by emission detection through time resolution (pulse delay) or phase modulation. Energy transfer can be detected by donor quenching or, preferably acceptor luminescense. A more detailed description of these lanthanide chelates and acceptor donor pairs may be found in U.S. Pat. No. 5,639,615, the entire contents of which is incorporated herein by reference.

Another aspect of the invention relates to a biomolecular sensor including semiconductor crystals or quantum well structures that are attached to a surface or embedded in a surface of a reaction vessel such as a microplate well or a microfluidics device. In an alternative embodiment, the donors and acceptors are positioned in space instead of on a surface. For example, they can be part of a three dimensional structure or embedded in such structures. One way of manufacturing such structures may include attaching a porous membrane to a conductive substrate and filling the pores by a suitable technique such as electrodeposition. Other suitable deposition methods include sputtering, metal evaporation, and chemical vapor deposition. Another way of providing such structures on the surface of a substrate includes depositing a polymeric membrane (e.g., polymethylmethacrylate) onto an appropriate conductive substrate and piercing the membrane with an electron beam, etching techniques or high energy particles. The affected areas of the polymeric membrane can then be dissolved with a solvent and metal can be deposited in the resulting pores. The remaining polymeric membrane can be removed with solvent. After formation of the structures, quantum well structures can formed on the surfaces using an electrochemical/chemical process for forming quantum dots. Such techniques are described in Penner, R. M, "Hybrid Electrochemical/Chemical Synthesis of Quantum Dots," Accounts of Echmical Research, 33, pp. 78–86 (2000), the contents of which are incorporated herein by reference. Other suitable techniques for forming these structures may include reactive ion etching of a substrate including a plurality of metal islands, or impregnating quantum dots into a porous material, for example, a porous glass such as Vycor™ available from Corning, Inc., Corning, N.Y. Still another technique for forming quantum dots on a surface in accordance with the present invention involves pulsing a bias voltage on a scanning probe microscope tip to remove and deposit material from a conductive surface. For example, copper material can be deposited onto a gold surface. Such techniques are describe in S. Hong and C. A. Mirkin, "A Nanoplotter with Both Parallel and Serial Writing Capabilities," 288 Science, pp. 1808–1811 (2000), the entire contents of which are incorporated herein by reference. Equally applicable to planar substrates is the quantum dot electrochemical/chemical synthesis procedures described earlier.

It will be apparent to those skilled in the art that various modifications and variations can be made to the present invention without departing from the spirit or scope of the invention. For example, a variety of donor and acceptor structures may be provided in accordance with the present invention. Thus, it is intended that the present invention cover modifications and variations of this invention provided they come within the scope of the appended claims and their equivalents.

What is claimed is:

1. A sensor comprising:
   a donor for emitting energy and an acceptor for receiving energy;
   a sensing area disposed between the donor and the acceptor;
   a photon source for directing photons towards the donor; and
   a detector for monitoring energy transfer between the acceptor and the donor as a function of the change in refractive index proximate the sensing area.

2. The sensor of claim 1, wherein the donor and the acceptor include dye molecules.

3. The sensor of claim 1, wherein the donor and the acceptor include a quantum well structure.

4. The sensor of claim 1, wherein the donor and the acceptor include fluorescent beads.

5. The sensor of claim 1, wherein the donor and the acceptor are selected from the group consisting of a fluorescent protein, a semiconductor, an atom, and a non-luminescent chromophore having a no-zero transition dipole moment.

6. The sensor of claim 1, wherein the sensor is adapted to detect interactions between biomolecules.

7. A sensor comprising:

a photon source;

a donor and an acceptor pair;

an area between the donor and the acceptor; and means for monitoring the energy transfer between the donor and the acceptor as a function of the change in refractive index of the sensing area.

8. A method of sensing the refractive index change on a surface comprising:

providing sensing area and a donor and an acceptor on the surface;

illuminating at least the donor;

monitoring the resonance energy transfer between an acceptor and a donor; and correlating the change in resonance energy transfer with a change in refractive index.

9. The method of claim 8, wherein the acceptor and the donor include a quantum well structure.

10. The method of claim 8, wherein the acceptor and the donor include a fluorescent dye.

11. The method of claim 8, wherein the acceptor and the donor are selected from the group consisting of a fluorescent protein, an atom and a luminescent chromophore having a non-zero transition dipole moment.

12. A method providing a biomolecular sensor comprising:

providing an acceptor and donor pair having a sensing area disposed therebetween;

directing photon energy towards the donor;

providing biomolecules proximate the sensing area; and monitoring the transfer of photon energy between the donor and the acceptor as a function of refractive index proximate the sensing area.

13. The method of claim 12, wherein the donor and acceptor pair include a quantum well structure.

14. The method of claim 12, wherein the donor and acceptor pair are selected from the group consisting of a fluorescent dye, a semiconductor, an atom or a luminescent chromophore having a non-zero transition dipole moment.

15. A biosensor comprising:

a substrate including donor and acceptor pair disposed on a surface of the substrate;

a sensing area disposed between the donor and the acceptor;

a photon source for directing photon energy towards the donor;

means for detecting energy transfer between the donor and the acceptor; and means for correlating the energy transfer with a change in refractive index proximate the sensing area.

16. The biosensor of claim 15, wherein the substrate includes a microplate well.

17. The biosensor of claim 15, wherein the substrate includes a glass slide including biomolecules attached thereto.

18. The biosensor of claim 15, wherein the substrate includes a microfluidics channel.

19. A method of manufacturing a sensor comprising:

providing an acceptor, a donor and a sensing area disposed therebetween on a surface;

directing energy towards the donor;

contacting the sensor with a solution;

monitoring the energy transfer between the acceptor and the donor as a function of the change in refractive index within the sensing area.

20. The method of claim 19, wherein the step of providing an acceptor, donor and sensing area on a surface further includes providing a three-dimensional porous structure having acceptors and donors disposed to provide a sensing volume.

* * * * *

UNITED STATES PATENT AND TRADEMARK OFFICE
CERTIFICATE OF CORRECTION

PATENT NO. : 6,542,229 B1
DATED : April 1, 2003
INVENTOR(S) : Peter J. Kalal et al.

It is certified that error appears in the above-identified patent and that said Letters Patent is hereby corrected as shown below:

<u>Column 9,</u>
Line 13, please delete "an" and change to -- the --

Signed and Sealed this

Seventeenth Day of February, 2004

JON W. DUDAS
*Acting Director of the United States Patent and Trademark Office*